United States Patent [19]
Abboudi

[11] Patent Number: 5,849,012
[45] Date of Patent: Dec. 15, 1998

[54] SURGICAL CLAMPING ASSEMBLIES AND METHODS OF USE

[76] Inventor: Shalom Y. Abboudi, 126 N. 9th Ave., Highland Park, N.J. 08904

[21] Appl. No.: 613,486

[22] Filed: Mar. 11, 1996

[51] Int. Cl.[6] .................................................. A61B 17/58
[52] U.S. Cl. ............................... 606/57; 606/54; 606/69; 606/70; 606/71; 606/74; 606/86; 606/105; 606/205
[58] Field of Search .................................. 606/54, 57, 60, 606/61, 69, 70, 71, 72, 74, 86, 103, 105, 205, 206, 207, 208

[56] References Cited

U.S. PATENT DOCUMENTS

| | | | |
|---|---|---|---|
| 3,960,147 | 6/1976 | Murray | 606/105 |
| 4,275,490 | 6/1981 | Bivins | 606/72 |
| 4,790,303 | 12/1988 | Steffee | 606/72 |
| 5,053,039 | 10/1991 | Hofmann et al. | 606/86 |
| 5,649,925 | 7/1997 | Barbera Alacreu | 606/103 |

FOREIGN PATENT DOCUMENTS

| | | | |
|---|---|---|---|
| 3630-138-A | 3/1988 | Germany | 606/105 |
| 1618-401-A | 1/1991 | U.S.S.R. | 606/105 |

*Primary Examiner*—Michael Powell Buiz
*Assistant Examiner*—Daphna Shai

[57] ABSTRACT

For clamping together two split halves of, for example, a sternum at the conclusion of open heart surgery, two clamping plates are secured to respective halves of the sternum in facing relationship across the meeting surfaces of the two halves. Each plate is secured to a respective half in spaced relation from the meeting surfaces. In one arrangement, each plate is secured by a rearwardly placed hook which extends along a respective side of the sternum and which preferably includes a spike which extends into the sternum through the side surface. In another arrangement, each clamping plate is secured by screws passing directly through the plate and into an underlying bone surface. In use, the jaws of a compressive pliers engage the two facing plates for pressing the two halves together. In one embodiment, while the plates are pressed together, a wire is wound around and between posts mounted on each plate for rigidly securing the plates together for maintaining the compressive force between the two halves. In another embodiment, while the plates are pressed together, a wire is wound through holes in the two facing plates for rigidly securing them together.

14 Claims, 3 Drawing Sheets

SURGICAL CLAMPING ASSEMBLIES AND METHODS OF USE

BACKGROUND OF THE INVENTION

This invention relates to surgical devices and particularly to clamping or fixation assemblies for holding together split sections of bone, particularly the sternum.

Surgical fixation of fractured bones has been well established and widely practiced in the medical community utilizing various techniques, including the use of surgical plates usually made of stainless steel. In this type of fixation, a plate of appropriate length, to span across a fracture, is placed on the outside of the bone and is fastened to the bone by means of screws drilled into the bone through preformed holes in the plate. Various arrangements have been utilized to compress the two bone ends at the fracture and hence promote healing. In addition to compression at the fractured ends of the bone, the plate also provides static (or rigid) stability.

Wires, usually made of stainless steel, have also been utilized surgically for fracture repair to compress bone ends. Wires are usually inserted either through holes in the bone, around the outside of the bone or around pins or screws inserted in the bone for added stability.

In open heart surgery, the sternum is longitudinally split in half and the rib cage pried open. After surgery, the two longitudinally extending sternal halves are compressed together along their cut surfaces and rigidly clamped together. With time, the two halves grow together to form a mechanically stable integral bone.

A flat bone, such as a sternum, provides some challenges for fixation utilizing conventional approaches. Plate and screw fixation is not practical because the bone is flat and soft. In addition, at the area of the sternum, there is not enough soft tissue padding in the front of the chest to cover over the screw heads. Moreover, in cases of emergency where the wound has to be re-opened, removal of the screws and plates can be time consuming.

A common technique currently employed for clamping the two sternal halves together is simply to wrap lengths of wire around the sternal halves at spaced points along the bone lengths. The wire ends are twisted around one another to tighten and secure the bone ends.

Problems encountered with this method include the difficulty of placing wire strands around the bone and tightening them. In addition, owing to normal movements of the rib cage and relative movements between the sternal halves until healing is complete, the wires can break or, more typically, cut into the bone tissue with resultant loss of fixation.

Other clamping arrangements have been developed including various belt wrapping systems which are buckled in place, thereby avoiding the need for multiple wire wrappings. Examples of such belt clamps are shown in U.S. Pat. Nos. 4,813,416 and 5,339,870, the subject matter of which are incorporated herein by reference.

While these belt systems provide some improvements over twisted wires, particularly in that they are stronger and reduce cutting into the bone tissue, such belt systems tend to be bulkier in size than simple lengths of wire and therefore more noticeable and objectionable by the patient.

SUMMARY OF THE INVENTION

A clamping assembly comprises two separate plates for mounting one each on respective sections of a cut bone. Neither plate is to span the area where the bone sections are to be joined together and means are promoted for rigidly and securely fastening each plate to a respective bone section without regard to the spatial relationship between the two bone sections.

According to a first embodiment of the invention, each plate includes, at one end, one or more dependent hooks and, at an opposite end, a pair of clamp engagement means. One engagement means comprises an aperture through the flat plate, and the other comprises a vertically extending post, preferably in the form of an inverted L.

In use of a clamp assembly, according to the first embodiment, the two halves of the bone to be fixed are compressed together at their previously cut surfaces to form a unitary bone having a common surface spanning the joint between the two severed surfaces and generally perpendicular thereto. The two flat plates are placed on the common surface in alignment with one another and on opposite sides of the joint. The clamps are each secured to a bone section by means of, for example, the clamp dependent hooks penetrating into a bone half through its side surface or going around the full thickness of the bone. The two plates are then engaged by the jaws of a pair of pliers, as by inserting the jaw ends into the plate apertures, and the two plates are forcibly pulled towards one another by the pliers for tightly squeezing together the bone halves. While the bone halves are so compressed together, the two plates are rigidly secured together by wrapping a wire around and between the two vertically extending posts and tieing the wire in place. The clamping pliers are then removed.

According to a second embodiment of the invention, each plate is as afore-described but without any dependent hooks. Rather, drill holes are provided through the plates for passage of screws to screw the plates to the respective bone sections. The use of the clamping assembly is as afore-described except that the plates are secured to the bone halves by screws, rather than by dependent hooks.

DESCRIPTION OF PREFERRED EMBODIMENTS

Figure 1:
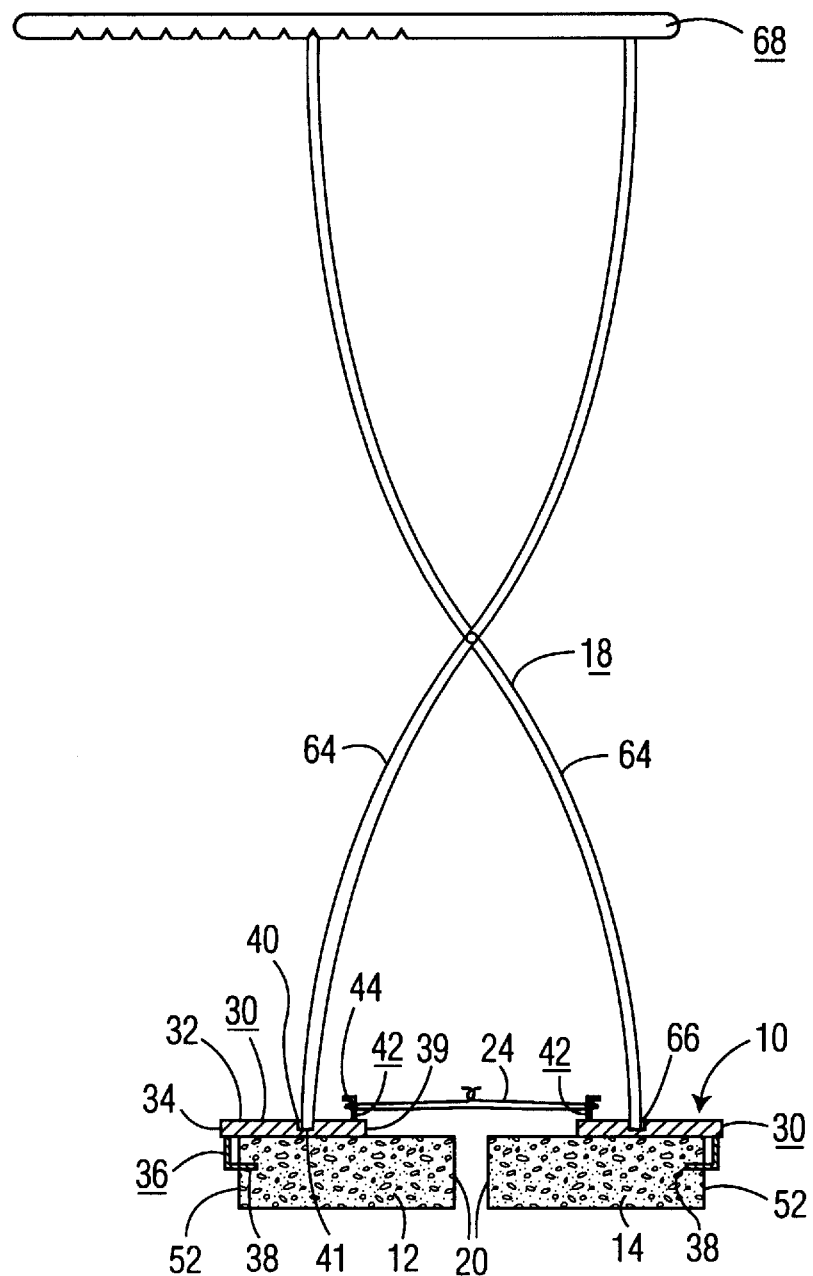
FIG. 1 is a side section of an assembled clamping assembly in accordance with this invention and further illustrating how the assembly is applied and secured to a pair of sternal halves being compressed together.

A clamping assembly 10 in accordance with a first embodiment of this invention, ideal for fixing flat bones such as the sternum, is shown in FIG. 1. This figure shows the assembly fully in place for clamping together the two sections 12 and 14 of a sternum which had been previously split (e.g., sawed) along the extending length of the bone. FIG. 1 shows a side section of the sternum which is elongated in a direction perpendicular to the plane of the drawing.

As illustrated, a compression pliers 18 is still in place in the process of compressing the two sternal halves against one another. For ease of illustration, the two surfaces 20 of the sternal halves which are being compressed together are shown spaced apart. However, in the condition being illustrated (including a tightening wire 24 already in place) the two surfaces are actually tightly pressed against one another.

Figure 2:
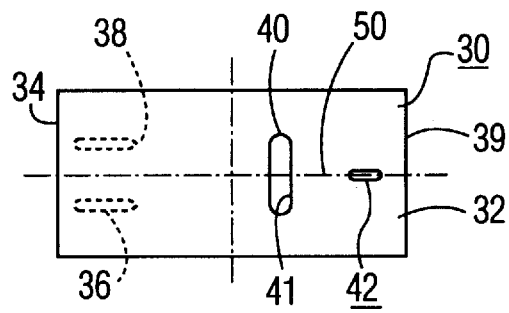
FIG. 2 is a plan view of one of the two clamps of the assembly shown in FIG. 1 but without a clamp assembly securing wire.

The clamping assembly 10 includes two identical clamps 30. A plan view of one such clamp 30 is shown in FIG. 2. Each clamp 30 comprises a generally flat plate 32 of a rigid material, e.g., stainless steel, ceramic or plastic. For use with an adult human, for clamping together split sternal halves, the plates 32 typically have a length of approximately one inch, a width of approximately one inch, and a thickness of approximately one sixteenth of an inch. The length, width and thickness of the plates may be varied depending on the material used for the plate.

Dependent from a "rear" side 34 of the flat plate 32 are one or more L-shaped hooks 36 (two hooks 36 being shown in FIG. 2). As shown in FIG. 1, the two clamps 30 face towards one another and it is convenient to refer to "rear" (or "lateral") and "front" (or "midline") portions of the clamps 30. The hooks 36, in this embodiment are integral extensions of, and of the same material as, the plates 32 and terminate in pointed spikes 38 for penetration into the sternal bone, as shown.

The midline side 39 of each clamp 30 includes two clamp engagement means; one being an aperture 40 entirely through the flat plate 32 and the other being a vertically extending post 42 having a lateralward bent end 44. The post 42 is disposed between the aperture 40 and the midline edge of the plate 32.

Completing the clamping assembly 30 illustrated in FIG. 1 is the previously mentioned tightening wire 24 which is tightly wrapped and secured around the two posts 42 for maintaining the clamps 30 in tightly clamped relationship with the sternal halves 12 and 14.

The mounting and securing of the clamping assembly 10 to the sternal sections 12 and 14 is now described. Prior to mounting of the clamping assembly 10, the two sternal halves are brought together and held in place, e.g., by hand or by a known surgical clamping instrument. Then, successive clamping assemblies 10 are applied at spaced intervals along the length of the sternum. FIG. 1 shows one such assembly. First, the two clamps 30 of each assembly 10 are placed on respective sternal halves on opposite sides of the joint to be formed by two facing surfaces 20 of the sternal halves 12 and 14. The two clamps 30 are carefully aligned with one another such that center lines 50 (FIG. 2) of the two clamps passing through the posts 42 are co-linear and perpendicular to the plane of the facing surfaces 20.

It will be appreciated that, owing to irregularities in the shape of the sternal sections 12 and 14 and the facing surfaces 20 along the sternum length, the terms "co-linear", "perpendicular", "planes" and the like are meant merely as approximations of the actual condition. Also, the placement of the clamps 30 of each assembly 10 can be entirely by eye, and small misalignments between the two clamps 30 are readily tolerated.

As shown in FIG. 1, the clamp spikes 38 penetrate into the sides 52 of the sternum halves 12 and 14. Depending upon the material and sharpness of the spikes, the spikes 38 can be forced into the sternum sides 52 by hand as the clamps 30 are mounted in place. Alternatively, extending holes can be pre-formed in the sternal halves through the side surfaces 52 using suitable pointed tools, e.g., a single tool including two sharply pointed members for providing two holes spaced apart in correspondence with the spacing between the two spikes 38 of each clamp 30.

With the clamp spikes 38 extending directly into the sternal sections, the clamps 30 are quite rigidly attached to the sternum halves. (If the spikes are inserted into preformed holes, a snug spike-hole fit is preferably provided by use of slightly undersized hole diameters or tapered spike walls or the like.)

The spikes 38 shown in FIG. 1 are the preferred embodiment because of the simplicity and reduced parts inventory. However, other means of securing the plates to the bones may be used.

Figure 3:
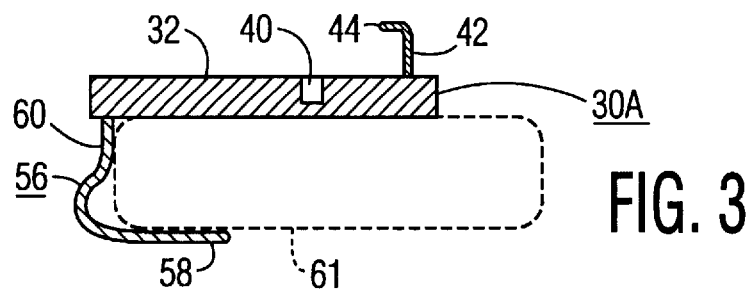
FIGS. 3–8 are side sectional views of clamps in accordance with other embodiments of the invention.

A further clamp embodiment 30A is shown in FIG. 3. Here, one or more wire hooks 56 (or an L-shaped plate) extend the entire thickness (the vertical dimension, as illustrated) of the sternal section and each hook 56 includes a forwardly extending arm 58 engaged with the bottom surface 61 of a sternal section. In effect, the clamp 30A shown in FIG. 3 is of U or C-shape including two generally parallel arms 32 and 58 connected by a side member 60. Owing to dimensional variations from patient to patient, as well as dimensional variations along the length of a single sternum, consideration must be given, using clamps 30A of the type shown in FIG. 3, for obtaining a reasonably snug fit of the clamps to the sternum. A kit of varying dimension clamps can be provided, for example, and proper fitting clamps are mounted on a trial and error basis. Alternatively, and as illustrated in FIG. 3, the clamp 30A is made of flexible material and appropriately shaped to allow spring clamping fit of identically dimensioned clamps 30A to differently dimensioned sternum sections.

Again, because of greater simplicity and the assurance of a quite firm engagement of the clamps to the sternum section and to decrease the required inventory of the units in the operating field, clamps 30 (FIGS. 1 and 2) including sternum penetrating spikes 38 are likely alternatives.

A feature of the invention is that each clamp 30 is mounted on a respective sternal half independently of the mounting of the other clamp. That is, while the two clamps 30 are carefully aligned with one another, neither clamp extends over both sternal sections and neither clamp directly spans the surfaces 20 of the sternal sections. An advantage of this is that the fit of each clamp with its respective sternal half is independent of any surface irregularities of the two sternal halves relative to one another. Specifically, the two clamps on opposite sides of the surfaces 20 need not be coplanar, thereby enabling each clamp to be securely fastened to its respective sternal half, regardless of variations from coplanarity of the sternal upper surfaces.

With a pair of clamps 30 mounted in aligned relationship on respective sternal halves as shown in FIG. 1, a mechanical compression applying means is used for tightly pressing the sternal sections against one another. Different compression applying means can be used, but owing to surface irregularities of the split sternum, it may be desirable to apply the compressive forces as closely as possible to those points along the sternum where the sternum sections are actually mechanically fastened together. To this end, the aforementioned aperture 40 is provided in each clamp as a simple means for providing a vertical wall 41 by means of which each clamp 30 can be securely engaged by a compressive stress applying mechanism.

In FIG. 1, a pliers 18 is used comprising a pair of jaws 64 having ends 66 dimensioned to fit into the clamp apertures 40 and into firm engagement with the aperture walls 41. Thus, upon squeezing the pliers handles, the clamps 30 are forced towards one another thereby firmly squeezing together the two sternal sections. As illustrated in FIG. 1, a simple ratchet mechanism 68 is used for locking the pliers in place at a selected level of compressive force.

Then, the two clamps 30 are firmly secured together for maintaining the compressive force, and the pliers is then removed. A quite simple securing means is a wire 24 of stainless steel or nylon or other like material which is wound between the two vertical posts 42 on the respective clamps 30. The bent ends 44 of the posts 42 simplify the wire wrapping process and prevent the wire from slipping off the posts.

As indicated in FIG. 1, the pliers 18 is relatively large in comparison with the clamping assembly 10 for allowing free access to the posts 42 for the wire wrapping process. To further facilitate application of the wire 42, the posts are disposed closer to the midline than the apertures 40, therefore allowing the operator to work between the inside of the pair of jaws 64 of the pliers. The wound wire is secured by twisting the ends of the wire around one another or by tieing the wire ends to the posts 42. (Conveniently, only one end need be tied, the other end including a loop which is slipped over one post at the beginning of the wrapping process.) It should also be appreciated that the ends 66 of the pliers may be applied to the rear sides 34 of the plates 32 where more room is needed t o wrap the wire around the posts.

After the wire wrapping and wire securing process, the pliers is removed. Clamping assemblies are used, as described, at spaced apart intervals along the elongated sternum for firmly securing the two sections together.

The clamps 30 are made large enough and of sufficiently sturdy materials to withstand the applied compressive stresses. The clamps can be formed of known rigid ceramics or plastic and, for greater strength, can comprise a steel plate 70 (FIG. 4) extending between and rigidly secured to (or integrated with) the oppositely disposed vertical post 42 and dependent hooks 36.

Figure 5:
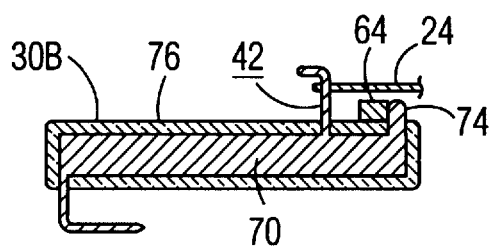

The apertures 40 through the clamp plates 32 tend to weaken the plates, and an alternative arrangement shown in FIG. 5 is the provision of an extending ridge or wall 74 for engagement by the pliers. While an extending wall can be used in direct replacement of the aperture 40 shown in FIGS. 1–3 (i.e., being an integral part of the flat plate 32 illustrated), in FIG. 5, the wall 74 is integral with a steel plate 70 embedded within a ceramic plate 76. As indicated in FIG. 5, during mounting of the clamp 30B on a sternal section, the pliers jaws 64 are disposed horizontally relative to the clamping assembly (rather than vertically as shown in FIG. 1). That is, the pliers jaws extend perpendicular to the plane of the FIG. 5 drawing when in place.

During wire wrapping, the wire 24 is wrapped between the posts 42 at a level above the walls 74 to which the pliers jaws are engaged and, after the wire is in place, the pliers jaws are slid out from under the wound wire.

Figure 6:
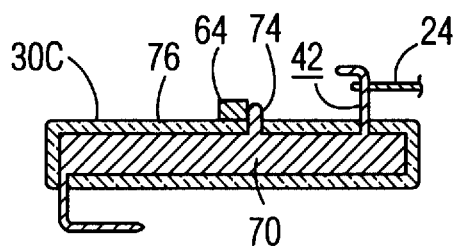

In FIG. 6, a clamp 30C is shown which is identical to the clamp 30B shown in shown in FIG. 5, except that the wall 74 is positioned lateralward to the post 42 rather than toward midline as shown in the clamp 30B. An advantage of the lateralward positioning of the wall 74 is that it provides freer access to the post 42, for wrapping the wire 24 therearound, when the jaw 64 of the clamping pliers 18 is in place.

A further advantage of the invention, and particularly in comparison with the prior art wire and belt arrangements which are in direct and compressive engagement with the bone surface, is that the securing wire 24 (FIG. 1), which extends between the two vertically extending posts 42, is not engaged with any of the surfaces of the sternal halves and, indeed, is likely at least slightly spaced above the bone surfaces. Accordingly, in those situations where it is necessary to re-enter the chest cavity and particularly in an emergency situation, the clamping assemblies 10 can be easily and quickly removed by cutting through the wrapping wire.

Figure 4:
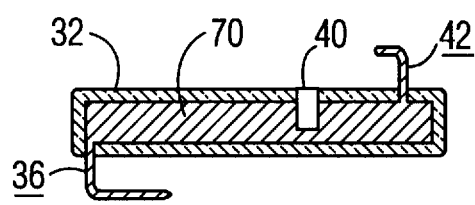
Figure 7:
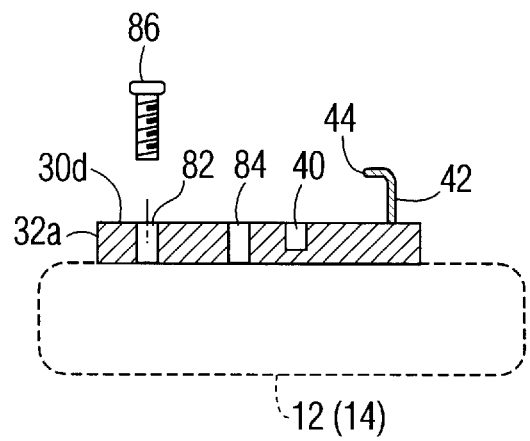

As previously explained, the use of dependent hooks (such as shown in FIG. 4) is a highly desirable arrangement for securing the clamps to the respective bone halves. FIG. 7 shows an alternative arrangement wherein dependent hooks are not used. Rather, one, and preferably two or more openings (screw holes) 82, 84 are provided through a plate 32a of a clamp 30D. Screws 86 of appropriate length are used to secure each clamp to a respective bone section. Thus, plate 32a would be similar to plate 32, except for the elimination of dependent hooks or extension arms to secure the plate to a bone section. As for the previously discussed embodiments, plate 32a includes post(s) 42 for enabling wires 24 to be connected between plates located on respective sections of the sternum. Plate 32a also includes an aperture 40 for enabling the plates and the underlying bone sections to be compressed. As noted before, the plates may be also compressed by applying pressure to the "rear" end of the plate.

Figure 8:
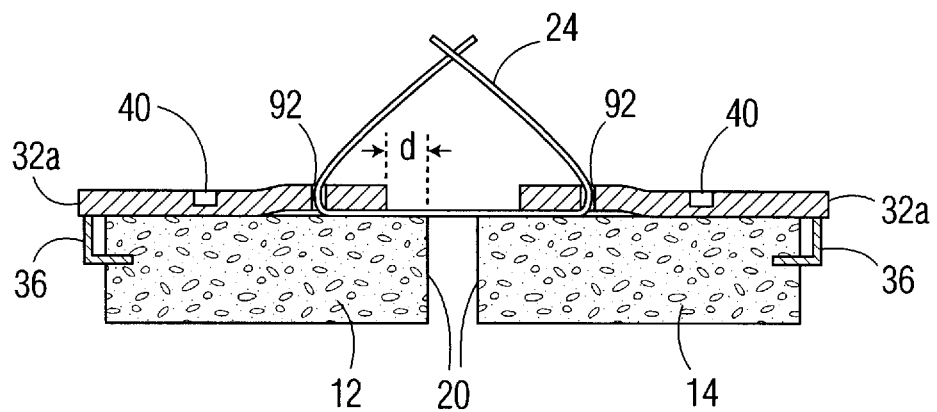

FIG. 8 shows an embodiment in which the need for posts 42 is eliminated. In FIG. 8, the plates 32a include preformed holes 92 through which a wire 24 can be passed and then tightened, such as by twisting. The plates 32a are shown to be secured to their respective bone sections by dependent hooks 36. However, the plates 32a may also be secured by extension arms 56 or by means of screw holes and screws, as shown in FIG. 7. As in the other embodiments of the invention, the front edge of each plate 32a is spaced a distance "d" in back of the bone break line 20. The plates 32a are also shown to include apertures 40. However, as noted above, the plates and the underlying bone may be compressed by applying pressure to the rear end of the plates. An obvious advantage of the embodiment of FIG. 8 is that the posts 42 are eliminated. Furthermore, the wire 24, when properly tightened, tends to pull the bone sections laterally with little, if any, upward thrust, thus providing for a good meshing of the underlying bone sections.

What is claimed is:

1. A clamping assembly for clamping together two sections of a bone having, when so clamped, a common surface generally perpendicular to contacting surfaces of the two bone sections, and each bone section having a side surface generally parallel to said contacting surfaces and transversely joined to said common surface, the assembly comprising a pair of plates for disposition on said common surface on respective ones of said bone sections and in alignment with one another within a plane generally perpendicular to said contacting surfaces and in spaced, non-overlapping relationship to said contacting surfaces; means for securing each one of said plates to a respective section of bone, and a wire positioned in contact with said plates above said common surface and above the lower surface of said plates for pulling said plates toward each other and for compressing the two bone sections together without the wire touching the common surface underneath the plates.

2. A clamping assembly as claimed in claim 1 wherein said means for securing each one of said plates to a respective bone section includes a hook extending from said plate and for engagement either inside the bone or around the outside of the bone with said side surface for securing each plate to its respective bone section.

3. A clamping assembly according to claim 2 wherein said hook of each one of said plates includes a first section generally perpendicular to said plate for extending along said bone side surface and a second section extending generally perpendicular to said first section for directly engaging a portion of said bone disposed between said second section and said plate for securing said plate to said bone.

4. A clamping assembly according to claim 3 wherein said second section comprises a spike for penetrating into said bone through said side surface thereof.

5. A clamping assembly as claimed in claim 1 wherein said means for securing each one of said plates to a respective bone section includes a screw extending through the plate and into the underlying bone section for securing each plate to its respective bone section.

6. A clamping assembly as claimed in claim 1 wherein each one of said plates includes a post projecting generally perpendicular to said plate in a direction away from the underlying bone section; and wherein said wire is connected between the posts for pulling the two plates together.

7. A clamping assembly according to claim 1 wherein each of said plates includes clamping jaw engageable means for enabling the application of tensile stresses through each said plate between said jaw engageable means and said hook.

8. A clamping assembly according to claim 7 wherein each of said plates includes a first surface for being in parallel relationship with said common surface when said plate is disposed on said common surface, and said engageable means comprises a wall projecting generally perpendicular to said first surface and extending generally parallel to said contacting surfaces.

9. A clamping assembly according to claim 8 wherein said wall defines one side of a depression in said plate.

10. A method for clamping together two elongated bone sections of a split flat bone comprising the steps of pressing together facing surfaces of two flat bone sections for forming a joined together flat bone having a common surface generally perpendicular to said facing surfaces and a pair of oppositely disposed sides on respective ones of said bone sections generally parallel to said facing surfaces, placing a pair of clamping plates on respective bone sections and facing forwardly towards one another and aligned with one another in a plane generally perpendicular to said facing surfaces, securing said plates to said respective flat bone sections and in spaced, non-overlapping relationship with said facing surfaces by means of rearwardly facing hooks extending along respective sides of said bone sections, and compressively securing said two plates to one another by wrapping a wire around and between said plates without the wire touching the common surface underneath the plates.

11. A method according to claim 10 wherein said pressing together step includes rigidly engaging the jaws of a compression pliers with respective portions of each of said plates for forcing said plates towards one another, performing said wire wrapping step while said jaws are rigidly engaged with said plate portions, and disengaging said jaws after completion of said wire wrapping step.

12. A method according to claim 10 wherein said plate securing step comprises forcing of said hooks into respective sections through said side surfaces thereof.

13. A method according to claim 10 wherein said plate securing step comprises wrapping a wire around and between a pair of extending posts mounted on respective one of said plates.

14. A clamping assembly for clamping together first and second sections of a relatively flat bone cut along a line generally transverse to the two sections comprising:

first and second plates;

means for securing the first plate to a first bone section on one side of said line and means for securing the second plate to a second bone section opposite to said first plate on the other side of said cut line;

said first and second plates being set back from said cut line and generally aligned opposite each other;

a wire; and means for positioning the wire in contact with said plates, without contacting the bone section underneath the plates for winding the wire between the two plates and for pulling the two plates toward each other and simultaneously compressing the two bone sections together without the wire touching the bone surface underneath the plates.

* * * * *